United States Patent
Albadawi et al.

(10) Patent No.: US 10,152,947 B2
(45) Date of Patent: Dec. 11, 2018

(54) DISPLAY BRIGHTNESS UPDATING

(71) Applicant: Microsoft Technology Licensing, LLC, Redmond, WA (US)

(72) Inventors: Haithem Albadawi, Redmond, WA (US); Han Yee Mimi Fung, Bellevue, WA (US); Farah Shariff, Kirkland, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 99 days.

(21) Appl. No.: 15/092,301

(22) Filed: Apr. 6, 2016

(65) Prior Publication Data

US 2017/0294174 A1  Oct. 12, 2017

(51) Int. Cl.
 *G09G 5/10* (2006.01)
 *G06F 1/16* (2006.01)
 (Continued)

(52) U.S. Cl.
 CPC ........... *G09G 5/10* (2013.01); *A61B 5/02055* (2013.01); *A61B 5/742* (2013.01); *G01J 1/429* (2013.01); *G06F 1/163* (2013.01); *G06F 1/1684* (2013.01); *G06F 1/3265* (2013.01); *G06F 3/015* (2013.01); *A61B 5/002* (2013.01); *A61B 5/024* (2013.01); *A61B 5/1112* (2013.01); *A61B 5/1118* (2013.01); *A61B 5/681* (2013.01);
 (Continued)

(58) Field of Classification Search
 None
 See application file for complete search history.

(56) References Cited

U.S. PATENT DOCUMENTS

| 4,962,910 A | 10/1990 | Shimizu |
| 5,148,023 A | 9/1992 | Hayashi et al. |

(Continued)

FOREIGN PATENT DOCUMENTS

| WO | 2015028462 A1 | 3/2015 |
| WO | 2015047288 A1 | 4/2015 |
| WO | 2015065516 A1 | 5/2015 |

OTHER PUBLICATIONS

Zhou, P. et al., "IODetector: A Generic Service for Indoor Outdoor Detection," Proceedings of the 10th ACM Conference on Embedded Network Sensor Systems (SenSys'12), Nov. 6, 2012, Toronto, Ontario, 14 pages.

(Continued)

*Primary Examiner* — Stephen T Reed
(74) *Attorney, Agent, or Firm* — Alleman Hall Creasman & Tuttle LLP

(57) ABSTRACT

Computing devices and methods for controlling light output of a display are disclosed. In one example, a default brightness setting is set to an indoor light output level. A UV light sensor is activated to detect UV radiation levels. Based on determining that one or more of the UV radiation levels exceed a UV threshold, the default brightness setting is updated to correspond to an outdoor light output level that is greater than the indoor light output level. Without using information from an ambient light sensor, the display is activated from a deactivated state to illuminate at the updated default brightness setting corresponding to the outdoor light output level.

20 Claims, 6 Drawing Sheets

(51) Int. Cl.
*G06F 1/32* (2006.01)
*G06F 3/01* (2006.01)
*A61B 5/0205* (2006.01)
*G01J 1/42* (2006.01)
*A61B 5/00* (2006.01)
*A61B 5/024* (2006.01)
*A61B 5/11* (2006.01)

(52) U.S. Cl.
CPC ..... *A61B 5/6898* (2013.01); *A61B 2560/0242* (2013.01); *A61B 2562/0219* (2013.01); *G09G 2320/0626* (2013.01); *G09G 2320/0653* (2013.01); *G09G 2320/08* (2013.01); *G09G 2360/144* (2013.01)

(56) References Cited

U.S. PATENT DOCUMENTS

| | | | |
|---|---|---|---|
| 6,060,321 | A | 5/2000 | Hovorka |
| 7,567,245 | B2 | 7/2009 | Mamata |
| 8,493,370 | B2 | 7/2013 | Gettemy |
| 8,964,298 | B2 | 2/2015 | Haddick et al. |
| 9,068,887 | B1 | 6/2015 | Bennouri et al. |
| 2003/0150998 | A1 | 8/2003 | Shin et al. |
| 2005/0151728 | A1 | 7/2005 | Nenonen |
| 2006/0230108 | A1 | 10/2006 | Tatsuta et al. |
| 2006/0289779 | A1 | 12/2006 | Marmaropoulos |
| 2007/0097065 | A1 | 5/2007 | Kreek et al. |
| 2008/0117100 | A1 | 5/2008 | Wang et al. |
| 2009/0043504 | A1 | 2/2009 | Bandyopadhyay et al. |
| 2009/0180356 | A1 | 7/2009 | Fujisawa |
| 2011/0024307 | A1 | 2/2011 | Simpson et al. |
| 2011/0267492 | A1 | 11/2011 | Prentice et al. |
| 2012/0056745 | A1 | 3/2012 | Noguchi et al. |
| 2012/0326046 | A1 | 12/2012 | Aslam et al. |
| 2014/0099614 | A1* | 4/2014 | Hu .......... G09B 19/00 434/236 |
| 2014/0107493 | A1 | 4/2014 | Yuen et al. |
| 2014/0129560 | A1 | 5/2014 | Grokop et al. |
| 2014/0132158 | A1 | 5/2014 | Land et al. |
| 2014/0171068 | A1* | 6/2014 | Marti .......... G01S 1/047 455/427 |
| 2014/0198016 | A1* | 7/2014 | Hunt .......... G09G 3/36 345/5 |
| 2014/0279790 | A1 | 9/2014 | Ramachandran et al. |
| 2014/0374600 | A1 | 12/2014 | Gokingco et al. |
| 2015/0097731 | A1 | 4/2015 | Russell |
| 2015/0102208 | A1 | 4/2015 | Appelboom et al. |
| 2015/0124009 | A1* | 5/2015 | Jung .......... G09G 3/2007 345/694 |
| 2015/0243200 | A1 | 8/2015 | Pan |
| 2015/0277572 | A1 | 10/2015 | Verplaetse et al. |
| 2015/0342522 | A1 | 12/2015 | Justice et al. |
| 2015/0342525 | A1 | 12/2015 | Justice et al. |
| 2015/0342552 | A1 | 12/2015 | Black |
| 2015/0346024 | A1 | 12/2015 | Hingorani et al. |
| 2016/0061657 | A1 | 3/2016 | Lapiere et al. |
| 2017/0118854 | A1 | 4/2017 | Dumont et al. |

OTHER PUBLICATIONS

Zhang, X. et al., "See UV on Your Skin: An Ultraviolet Sensing and Visualization System," Proceedings of the 8th International Conference on Body Area Networks (BodyNets '13), Sep. 30, 2013, Boston, Massachusetts, 7 pages.
"Adding UV Sensing to Wearables & Consumer Applications," Silicon Labs White Paper, Rev. 1.0, Available as Early as Jan. 1, 2014, 7 pages.
Griffiths, S., "The bracelet that prevents SUNBURN: $100 gadget tells you when to slap on sunscreen and warns when you've been out too long," Daily Mail MailOnline Website, Available Online at www.dailymail.co.uk/sciencetech/article-2537168/The-bracelet-stops-SUNBURN-100-gadget-tells-slap-sunscreen-warns-youve-long.html, Jan. 10, 2014, 21 pages.
"Barclays: Apple's 'iWatch' could include UV light exposure sensor," AppleInsider Website, Available Online at http://appleinsider.com/articles/14/04/07/barclays-apples-iwatch-could-include-uv-light-exposure-sensor, Apr. 7, 2014, 10 pages.
"SparkFun UV Sensor Breakout—ML8511," SparkFun Website, Available Online at www.sparkfun.com/products/12705, Available as Early as Mar. 30, 2015, Retrieved Sep. 4, 2015, 7 pages.
Frank, M., "The Microsoft Band Is the Wearable Nobody's Talking About," Outside Website, Available Online at www.outsideonline.com/1965931/microsoft%E2%80%99s-band-wearable-nobody%E2%80%99s-talking-about, Apr. 13, 2015, 9 pages.
ISA European Patent Office, International Search Report and Written Opinion Issued in PCT Application No. PCT/US2016/053856, dated Dec. 1, 2016, WIPO, 11 pages.
IPEA European Patent Office, Second Written Opinion Issued in PCT Application No. PCT/US2016/053856, dated Apr. 20, 2017, WIPO, 7 pages.
ISA European Patent Office, International Search Report and Written Opinion Issued in PCT Application No. PCT/US2017/024875, dated Jul. 3, 2017, WIPO, 23 pages.
IPEA European Patent Office, International Preliminary Report on Patentability Issued in PCT Application No. PCT/US2016/053856, dated Jul. 19, 2017, WIPO, 8 pages.
Ruddock, David, "Android "L" Feature Spotlight: Auto-Brightness Is Gone, "Adaptive Brightness" Takes Its Place", Published on: Jun. 26, 2014 Available at: http://www.androidpolice.com/2014/06/26/android-l-feature-spotlight-auto-brightness-is-gone-adaptive-brightness-takes-its-place/.
"Developments and trends of optical sensor technology and mobile product applications", Published on: Jul. 10, 2012 Available at: http://www.digitimes.com/supply_chain_window/story.asp?datepublish=2012/07/10&pages=VL&seq=202.

* cited by examiner

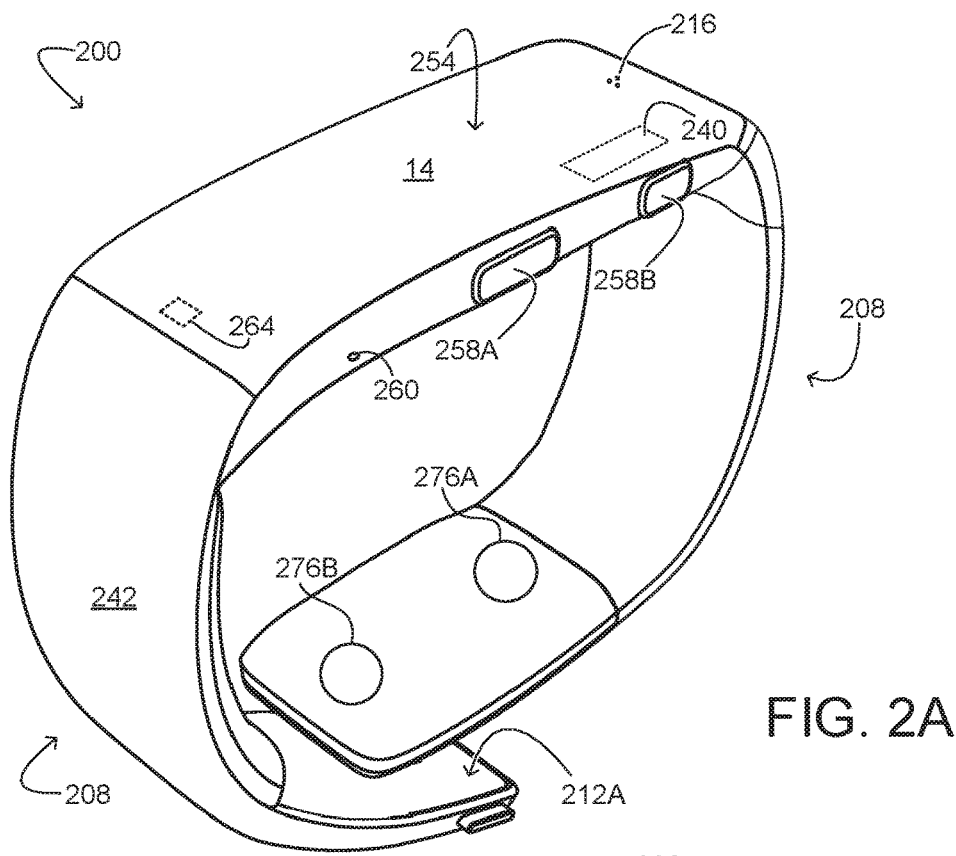
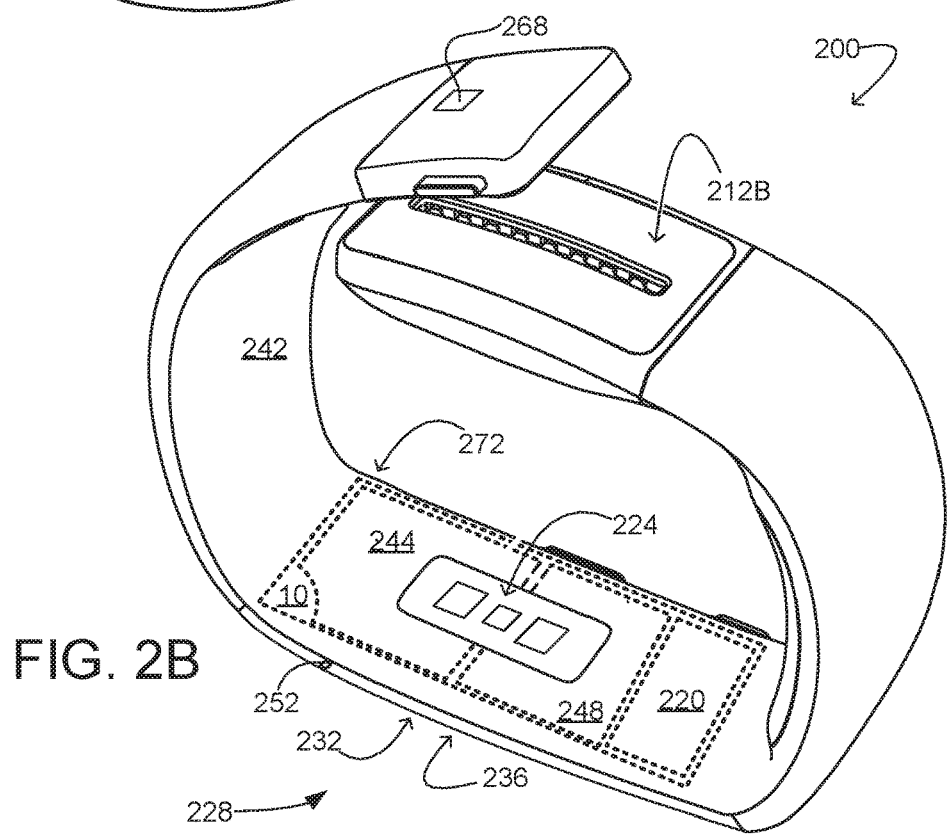

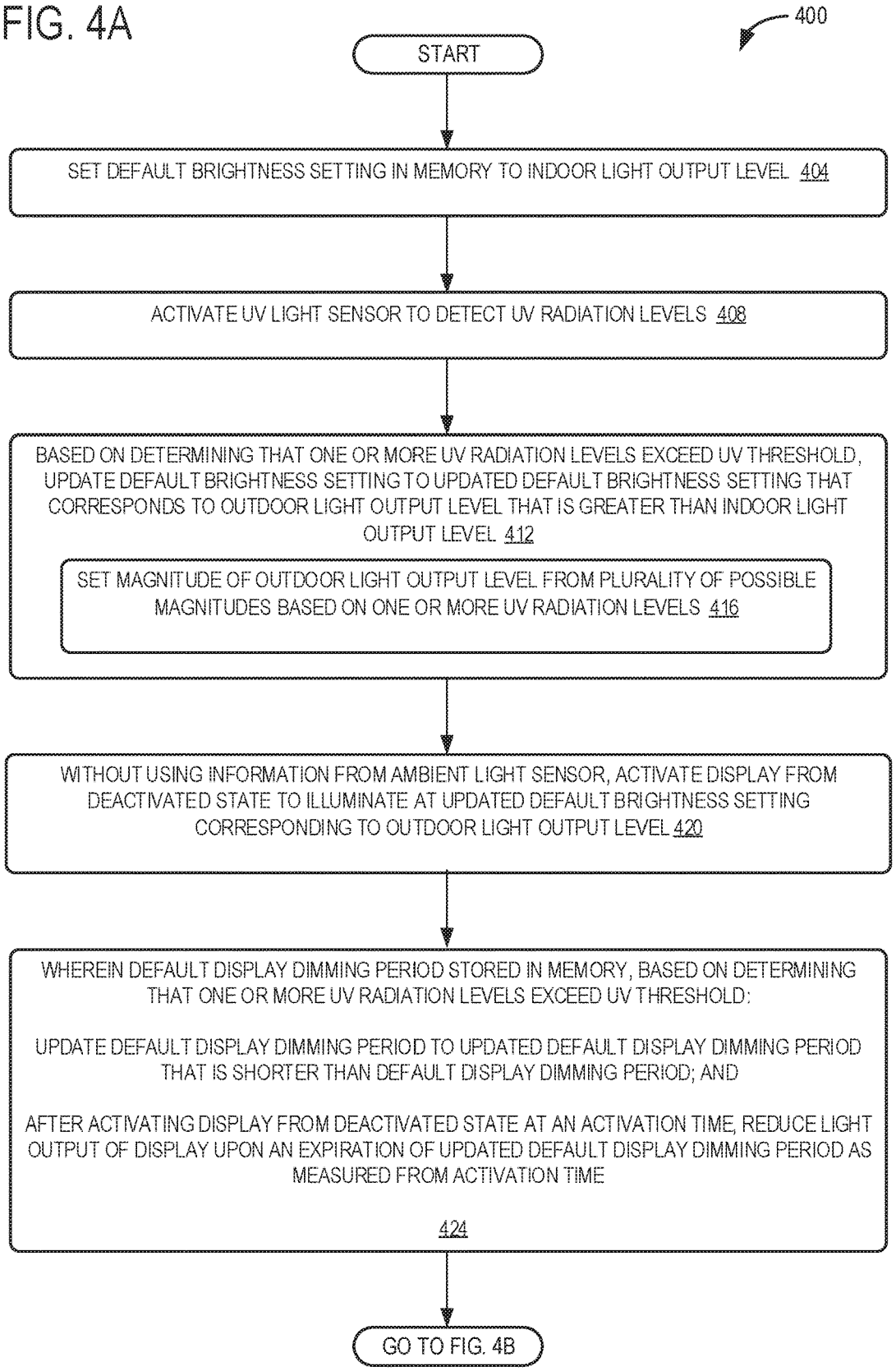

DISPLAY BRIGHTNESS UPDATING

BACKGROUND

Computing devices with displays may use an ambient light sensor to control display brightness. When the display is turned on, the ambient light sensor may analyze lighting conditions to adjust the brightness of the display.

SUMMARY

Computing devices and methods for controlling light output of a display are disclosed herein. In one example a computing device comprises a display, an ambient light sensor, a UV light sensor, and a memory storing a default brightness setting. A display brightness program sets the default brightness setting to an indoor light output level and activates the UV light sensor to detect UV radiation levels.

Based on determining that one or more of the UV radiation levels exceed a UV threshold, the default brightness setting is updated to correspond to an outdoor light output level that is greater than the indoor light output level. Without using information from the ambient light sensor, the display is activated from a deactivated state to illuminate at the updated default brightness setting corresponding to the outdoor light output level.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

FIGS. 2A and 2B show a wearable computing device according to examples of the present disclosure.

FIGS. 4A and 4B show a method for controlling light output of a display according to examples of the present disclosure.

DETAILED DESCRIPTION

Figure 1:
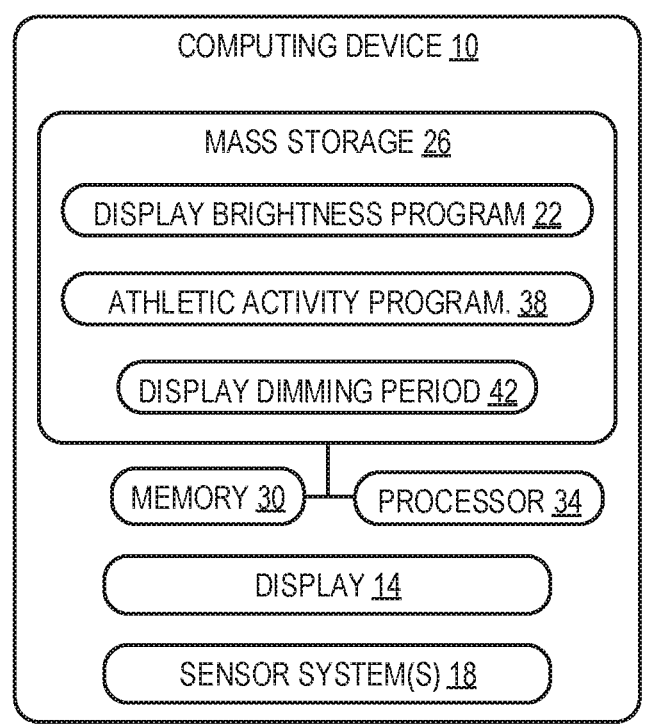
FIG. 1 is a schematic representation of a computing device according to examples of the present disclosure.

Computing devices with displays may be used in a variety of lighting conditions, ranging from darker indoor settings to brighter outdoor environments. Some devices may adjust a brightness of the display according to the ambient light levels detected by an ambient light sensor (ALS).

Portable computing devices also may include features directed to conserving battery life. For example, a display may be dimmed or turned off after a period of inactivity. Where the computing device includes a sensor, the sensor may be deactivated unless its data is being utilized. For example, an ALS on a smartphone may be deactivated when the display is turned off. When a user turns the phone on, the ALS may be activated to detect levels of ambient light.

In some examples, upon activation of the ALS a sequence of events may occur before the display brightness is adjusted. Execution of these events may result in a time lag between an ALS activation command and the actual adjustment of the display brightness. For example, upon activation the ALS may be energized and may begin to sample ambient lighting conditions at a sampling rate, such as 2 Hz. After recording and outputting a predetermined number of samples, such as 4 or 6 samples for example, a display brightness algorithm may compute a current lighting condition. Using the computed current lighting condition, the display brightness algorithm may then correspondingly adjust the brightness of the display by, for example, reducing the current drawn by the display. The display brightness may then be increased or decreased to match the current lighting condition.

In some examples, the time lag between the ALS activation command and the display brightness reaching the adjusted level may range from approximately 1-2 seconds to approximately 5-6 seconds or more. In some use case scenarios, even a 1-2 second delay in adjusting the screen brightness may cause an unsatisfactory user experience. For example, a runner may be wearing a wearable computing device that includes a display, such as a wrist-worn fitness tracker or running watch. The runner may be running outside on a bright sunny day with her fitness tracker display turned off to conserve battery life. To check her running pace she may activate the display by raising her wrist and tapping the display with a finger. The display may immediately activate at a default indoor light output level, perhaps as a battery-conservation measure. In one example, such indoor light output level may correspond to driving the display with a current of approximately 11 mA per hour.

In the bright sunlight the runner may have difficulty reading the text and/or images displayed at this indoor light output level. Additionally, while the ALS may subsequently adjust the display to a brighter light output level after several seconds, the runner may desire a faster response, especially while engaged in running. For example, holding the runner's arm and wrist in a raised position for reading the display may conflict with her natural running motion. Maintaining such a pose may be particularly challenging during high exertion portions of her run, such as sprinting or climbing a steep hill.

In another example, a smartphone user may be walking outside with his smartphone display turned off. An audible text message alert may sound indicating the receipt of a text message. The user may quickly raise his phone to a reading position as the display turns on. As the user struggles to read the message at the initial indoor light output level of the display, a several-second delay in adjusting the screen brightness may prove annoying. It will be appreciated the foregoing are merely examples, and that other use cases involving wearable devices and other computing device form factors in which a user may desire a quick adjustment of display light output level are contemplated by the present disclosure.

FIG. 1 illustrates a computing device 10 according to examples of the present disclosure. In different examples computing device 10 may take a variety of forms, such as a wrist-mounted device or other wearable computing device, smartphone, tablet, notebook or laptop computer, computerized medical device, such as a computerized pulse oximeter, electronic inhaler, blood pressure monitor, etc. Computing device 10 may be communicatively coupled to one or more other devices via a wired connection or a wireless connection to a network. In some examples, the network may take the form of a local area network (LAN), wide area network (WAN), wired network, wireless network, personal area network, or a combination thereof, and may include the Internet.

As schematically shown in FIG. 1, the computing device 10 may comprise a display 14. In different examples, the display 14 may comprise a liquid crystal display (LCD), such as a capacitive thin-film transistor (TFT) full color display, an active-matrix organic light-emitting diode (OLED) display, or any other suitable display technology. The display 14 may be a touch-screen display configured to receive touch input from a user, and may be resistive, capacitive, or optically based.

In some examples the computing device 10 may comprise one or more sensor systems 18 that may generate signals and other data responsive to detecting various inputs. Examples of sensor systems may include, for example, ambient light sensors (ALS), ultraviolet (UV) light sensors, heart rate monitors, accelerometers, gyroscopes, magnetometers, inertial measurement units (IMU), barometers, ambient temperature sensors, global positioning systems (GPS), microphones, galvanic skin response sensors, and skin temperature sensors.

The computing device 10 may comprise a display brightness program 22 stored in mass storage 26 The display brightness program 22 may be loaded into memory 30 and its instructions executed by processor 34 to perform one or more of the methods and processes for controlling light output of a display as described herein. One or more other applications may be stored in mass storage 26, such as an athletic activity program 38 described in more detail below. Additional data may be stored in mass storage 26, such as a display dimming period 42 described in more detail below.

With reference now to FIGS. 2A and 2B, aspects of an example computing device 10 in the form of a wearable computing device 200 will now be described. In this example wearable computing device 200 is band-shaped with fastening componentry 212A and 212B arranged at both ends of the device. The fastening componentry enables the device to be closed into a loop and to be worn on a user's wrist.

Wearable computing device 200 may include various functional components integrated into the device. For example, the wearable computing device 200 may include computing device 10, display 14, a loudspeaker 216, and a communication suite 220. The wearable computing device 200 also includes various sensors, such as an optical heart rate sensor 224 and motion sensing componentry. The optical heart rate sensor 224 may comprise an optical source configured to illuminate one or more blood vessels through a user's skin, and an optical sensor configured to measure reflected illumination from the blood vessels. In this manner, measurements of the wearer's heart rate, blood oxygen level, blood glucose level, or other biomarkers with optical properties may be generated.

In some examples the motion sensing componentry may comprise an accelerometer 232 and a gyroscope 236 inside the device 200. In other examples, the motion sensing componentry may comprise any combination of accelerometers, gyroscopes and magnetometers.

In some examples the accelerometer and gyroscope may furnish inertial and/or rotation rate data along three orthogonal axes, as well as rotational data about the three axes, for a combined six degrees of freedom (6 DOF). This 6 DOF sensory data may be used to provide pedometer and calorie-counting functions, for example.

The wearable computing device also may include a GPS receiver 240 for determining the wearer's geographic location and velocity. In some configurations, the antenna of the GPS receiver may be relatively flexible and extend into side regions 208. The wearable computing device 200 also may include a barometer 252 for measuring a barometric pressure to which the device is subject.

The above-described components may draw power from one or more energy-storage cells 242. Energy-storage cell(s) 242 may comprise one or more batteries, such as a lithium ion battery.

In wearable computing device 200, computing device 10 is situated below display 14 and operatively coupled to the display, along with loudspeaker 216, communication suite 220, and the various sensors. The computing device 10 includes a data-storage machine 244 to hold data and instructions, and a logic machine 248 to execute the instructions. Additional details regarding the components and computing aspects of the computing device 10 are described in more detail below with respect to FIG. 5.

Display 14 may be any suitable type of display. In some configurations, a thin, low-power light emitting diode (LED) array or a liquid-crystal display (LCD) array may be used. An LCD array may be backlit in some implementations. In other implementations, a reflective LCD array (e.g., a liquid crystal on silicon, LCOS array) may be front lit via ambient light. A curved or a flat display may be used. In some examples AMOLED displays or quantum dot displays may be used.

Communication suite 220 may include any appropriate wired or wireless communications componentry. The communication suite 220 may include two-way Bluetooth, Wi-Fi, cellular, near-field communication, and/or other radios. In some implementations, the communication suite 220 may include an additional transceiver for optical, line-of-sight (e.g., infrared) communication.

In wearable computing device 200, a touch-screen sensor 254 is coupled to display 14 and configured to receive touch input from the user. Pushbutton sensors may be used to detect the state of push buttons 258A, 258B which may include rockers. Input from the pushbutton sensors may be used to enact a home-key or on-off feature, control audio volume, turn the microphone on or off, or other function.

FIGS. 2A and 2B show various other sensors of wearable computing device 200. Such sensors include microphone 260. ALS 264, UV sensor 268, and ambient temperature sensor 272. The microphone 260 provides input to computing device 10 that may be used to measure the ambient sound level and/or sound pressure profiles, and may receive voice commands from the wearer. Input from one or more of the above-described sensors may be used to assess aspects of the wearer's environment, such as the whether the wearer is indoors or outdoors, temperature, overall lighting level, etc.

In some examples the UV sensor 268 may be utilized along with other related circuitry to detect a level of UV radiation in a particular area where the measurement is being taken. In some examples one or more measured UV radiation levels may be correlated to the UV index. The UV index is a number between 0 and 11+ that is linearly related to the intensity of sunburn-producing UV radiation in a particular area. UV index values above 11 indicate an extreme UV exposure condition.

A UV index value may be determined by measuring the strength of UV radiation for one or more wavelengths between 280 and 400 nm, which corresponds to the full spectrum of UVB (280-314 nm) and UVA (315-400 nm) radiation. Ozone in the atmosphere absorbs more of the shorter UV wavelengths than the longer wavelengths. Accordingly, the strength of ground-level UV radiation differs across the UV spectrum.

An example of determining a UV index value will now be described. UV strengths at different points along the UV spectrum may be determined. For example, UV strengths may be calculated for three different wavelengths along the spectrum. In one example, at a wavelength of 290 nm the UV strength may be 4, at 320 nm the UV strength may be 19, and at 400 nm the UV strength may be 23.

Next, an adjustment for the sensitivity of human skin to UV radiation may be incorporated. Shorter UV wavelengths cause more skin damage than longer UV wavelengths of the same intensity. Accordingly, a weighting function may be utilized to weight the calculated UV strength at each wavelength to account for this varying skin sensitivity. In some examples, the McKinlay-Diffey erythema action spectrum function may be utilized for such weighting.

Using such a weighting function, the skin response weighting factors for each of the UV wavelengths are multiplied by the ground-level UV strength measurements to yield an effective strength of the UV radiation at each wavelength. Continuing with the present example, a weighting factor for the 290 nm wavelength may be 15, a weighting factor for the 320 nm wavelength may be 5 and a weighting factor for the 400 nm wavelength may be 3. An effective UV strength at each wavelength may then be determined at each wavelength.

For example, at 290 nm the effective UV strength is 60 (4×15), at 320 nm the effective UV strength is 95 (19×5), and at 400 nm the effective UV strength is 69 (23×3). Next, the effective UV strength at each of these wavelengths is summed, giving a value that represents the total effect of UV radiation on skin. In the present example, the total UV effect is 224 (60+95+69). The total UV effect is then scaled by dividing it by 25 and rounding to the nearest whole number. The result is a number that usually ranges from 0 (darkness or very weak sunlight) to the mid-teens (very strong sunlight). In the present example the UV index would be 224/25=9. It also will be appreciated that any other suitable method for determining a UV index value may be utilized.

FIG. 2A shows a pair of contact sensor modules 276A and 276B that contact the wearer's skin when wearable computing device 200 is worn. The contact sensor modules may include independent or cooperating sensor elements to provide a plurality of sensory functions. For example, the contact sensor modules may provide an electrical resistance and/or capacitance sensory function, which measures the electrical resistance and/or capacitance of the wearer's skin. In some examples, a contact sensor module may also provide measurement of the wearer's skin temperature.

In some examples the computing device 10, via the sensory functions described herein, may be configured to acquire various forms of information about the wearer of wearable computing device 200. Such information would be acquired and used with utmost respect for the wearer's privacy. Accordingly, the sensory functions may be enacted subject to opt-in participation of the wearer. In implementations where personal data is collected on the device and transmitted to a remote system for processing, that data may be anonymized.

Example use cases illustrating aspects of the present disclosure will now be presented. While some examples are described below in the context of a wearable computing device, such as wearable computing device 200 described above, the principles of the present disclosure may be used with non-wearable computing devices and numerous different types and form factors of computing devices. Additionally and in some examples, the principles of the present disclosure may be used with computing devices that do not comprise an ALS.

As noted above and with reference to the example wearable computing device 200, in some examples the light output of display 14 may be controlled utilizing UV radiation levels detected by UV sensor 268. In some examples the UV sensor 268 and related circuitry may be programmatically activated and may operate in the background to detect UV radiation levels. The UV sensor 268 may operate at a sampling frequency of 0.1 Hz, 0.2 Hz., 0.3 Hz or any other suitable frequency. In some examples, the UV sensor 268 may be driven with a current of approximately 1.6 mA per hour. As described in more detail below, one or more UV radiation levels detected by the UV sensor 268 may be utilized to update a default brightness setting of the display 14.

Figure 3:
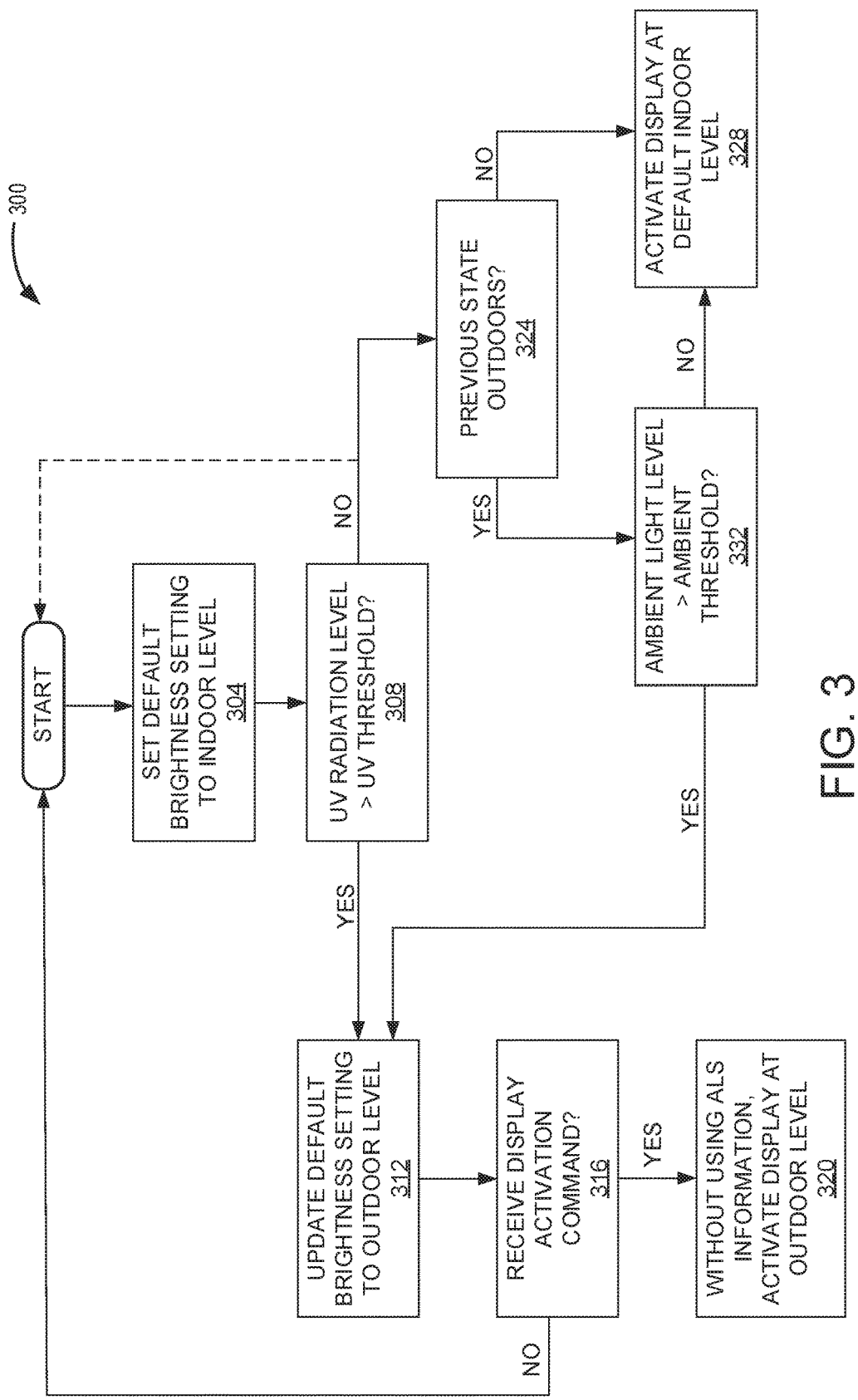
FIG. 3 shows a flow chart illustrating the use of a UV sensor to update a display brightness setting according to examples of the present disclosure.

With reference now to FIG. 3, a flow chart 300 illustrating the use of a UV sensor to update the brightness setting for a display according to examples of the present disclosure is provided. In some examples an ALS also may be utilized. At the Start of the flow chart 300, the UV sensor 268 of wearable computing device 200 may be activated and may detect UV radiation levels. The ALS 264 may be deactivated. In some examples and to conserve battery life, the ALS 264 may be normally deactivated whenever the display 14 is deactivated, and may be activated whenever a display activation command is received programmatically or via user input. Signals and/or other information related to ambient light levels may be received by computing device 10 from the ALS 264 and may be stored in data storage machine 244.

At 304 of flow chart 300 the default brightness setting may be set to an indoor light output level that may be generally suitable for indoor viewing of the display 14. In some examples the indoor light output level may correspond to driving the display 14 with a current of approximately 10 mA. The default brightness setting may be stored in data storage machine 244.

At 308 one or more of the UV radiation levels detected by UV sensor 264 may be compared to a predetermined UV threshold. In one example, the UV sensor 268 may measure UV radiation levels at a sampling rate of 0.2 Hz. (once each 5 seconds). At a predetermined comparison rate, such as 0.017 Hz (once each minute), one or more of the UV radiation levels may be compared to the predetermined UV threshold. In one particular example, the UV sensor 264 may sample the UV radiation level each 5 seconds over predetermined intervals of one minute. For each one minute interval, the peak measurement from the 12 samples over the interval is used as the selected UV radiation level to be compared to the predetermined UV threshold. In other examples, other suitable UV sensor sampling rates, comparison rates and predetermined intervals may be utilized. In other examples, different methods for determining a selected UV radiation level may be utilized, such as averaging the samples gathered over an interval.

Returning to 308, in different examples the predetermined UV threshold may be a discrete UV radiant flux (power) value expressed as watts per square meter ($W/m^2$), or other measure of a UV radiation level, such as a UV index value. In some examples, the UV threshold may be a UV index value of 1.0, 2.0, 3.0 or other suitable value.

If the UV radiation level exceeds the UV threshold, then it is determined that the wearable computing device 200 is outdoors. Accordingly and at 312, the display brightness program 12 updates the default brightness setting to an updated default brightness setting that corresponds to an outdoor light output level greater than the indoor light output level. In some examples the outdoor light output level may correspond to driving the display 14 with a current of approximately 20 mA.

At this point and in one potential advantage of the present disclosure, with the default brightness setting set to the outdoor light output level, as soon as the display 14 is activated it is illuminated at the outdoor light output level. Accordingly and at 316, when a display activation command is received either programmatically or from user input, the display is activated at the outdoor light output level without using information from the ALS 264 (at 320).

Thus and for example, where a user of the wearable computing device 200 walks outside from her dimly lit home into the afternoon sun, the display brightness program 12 may update the default brightness setting as described above. Accordingly, when the user subsequently taps the display 14 to view data, the display illuminates at the brighter outdoor light output level without using information from the ALS 264. In this manner the display 14 quickly illuminates at an easily-readable brightness level, and delays associated with utilizing the ALS 264 and/or analyzing information received from the ALS may be avoided.

Returning to 316, in some examples and after updating the default brightness setting, the display brightness program 12 may wait to receive a display activation command for a predetermined timeframe. In some examples the predetermined timeframe may correspond to the predetermined interval described above, such as one minute. Other suitable predetermined timeframes may be utilized. If a display activation command is not received during the predetermined timeframe, the flow chart 300 may return to the Start.

Returning to 308, in some example in which the computing device does not comprise an ALS, if the UV radiation level does not exceed the UV threshold, the flow chart 300 may return to the Start. In other examples such as wearable computing device 200 in which the device includes an ALS, an additional process may determine if the device is outdoors. For example, in some situations a wearer of the wearable computing device 200 may temporarily obscure or cover the UV sensor 268, such as by holding or resting the wearer's wrist against clothing, the wearer's leg or other surface. Though the wearer may still be outside, UV radiation levels measured by the UV sensor 268 may be interrupted.

Accordingly, at 324 the flow chart 300 may determine if a previous state of the device was outdoors. If the previous state of the device was not outdoors, then at 328 the display 14 may be activated at the default brightness setting that corresponds to an indoor light output level. If the previous state of the device was outdoors, then at 332 information from the ALS may be used to determine if an ambient light level is greater than a predetermined ambient light threshold. The predetermined ambient light threshold may correspond to a discrete ambient light radiant flux value expressed in $W/m^2$. Where the ambient light level is greater than the predetermined ambient light threshold, the flow chart 300 may proceed to 312. Where the ambient light level is not greater than the predetermined ambient light threshold, then at 328 the display 14 may be activated at the default brightness setting that corresponds to an indoor light output level.

In some examples, the display brightness program 12 may be configured to set a magnitude of the outdoor light output level from a plurality of possible magnitudes based on the one or more UV radiation levels. Alternatively expressed, the outdoor light output level may be set to continuously correspond with a current level of environmental brightness based on the UV radiation level measured by the UV sensor 268. For example, where the UV radiation level corresponds to a UV index value of 3, the magnitude of the outdoor light output level may be set to a value that corresponds to driving the display with a current of approximately 30 mA. Where the UV radiation level corresponds to a lower UV index value of 1, the magnitude of the outdoor light output level may be set to a lower value that corresponds to driving the display with a current of approximately 22 mA. In other examples, raw data from the UV sensor may be used to continuously adjust the magnitude of the outdoor light output level to correspond to the current level of environmental brightness.

In some examples in which the computing device comprises an ALS, the ALS may be utilized to confirm that the selected light output level for the display is correct. For example, an outdoor light output level may be selected based on a detected UV radiation level. Subsequently, the ALS may be activated and information from the ALS may indicate that the ambient light level is quite low, despite the UV radiation level being relatively high. For example, the user may be standing in a dimly lit room near a UV radiation source. In this example and using the ALS information, the display brightness program 12 may adjust the light output level to a lower value corresponding to an indoor setting.

In some examples and with reference again to FIG. 1, a default display dimming period 42 may be stored in the mass storage 26 of the computing device 10. In these examples and to conserve battery life, the display brightness program 12 may be configured to reduce a light output of the display 14 upon an expiration of the default display dimming period 42. In some examples when the display brightness program 12 determines that one or more UV radiation levels exceed the UV threshold, and thus the wearable computing device 200 is outdoors, the program may update the default display dimming period to an updated default display dimming period that is shorter than the default display dimming period.

For example, where the default display dimming period is 10 seconds, the updated default display dimming period may be 4 seconds. In these examples, after activating the display 14 from the deactivated state at an activation time, the display brightness program 12 may reduce a light output of the display upon the expiration of the updated default display dimming period as measured from the activation time. In this manner, battery life may be further conserved.

In some examples, after activating the display from the deactivated state, the UV sensor 268 may continue to sample the UV radiation levels. When one or more of the UV radiation levels do not exceed the UV threshold, the light output of the display 14 may be reduced to further conserve battery life.

In some examples, one or more other sensors may be utilized to trigger an update of the default brightness setting to the outdoor light output level. For example, a GPS system comprising GPS receiver 240 may receive and measure GPS signals of varying strength. As a general matter, GPS signals are stronger outdoors than indoors. Accordingly, in some examples the display brightness program 12 may be configured to, based on receiving a GPS signal from the GPS system that is above a predetermined signal threshold, update the default brightness setting to the updated default brightness setting corresponding to the outdoor light output level.

In some examples, movement of the wearable computing device 200 may be utilized to update the default brightness setting to a brighter light output level. For example, movement of the wearable computing device 200 at a velocity within a predetermined range of velocities, such as between 4 miles per hour (mph) and 10 mph, may indicate that the person is briskly walking or running. In many cases a person briskly walks or runs outdoors, especially over a sustained period. Accordingly, the display brightness program may be configured to, based on receiving location data from the GPS system that indicates a velocity of the device within a predetermined range of velocities, update the default brightness setting to the updated default brightness setting corresponding to the outdoor light output level.

Additionally and in some examples where the user is running indoors, such as on an indoor track, updating the default brightness setting to the updated default brightness setting corresponding to the outdoor light output level may still provide an improved user experience. For example, a user engaged in vigorous running may want to quickly check her current pace by glancing at the display 14 of her wearable computing device 200. In this case, illuminating the display at the brighter outdoor light output level, even if the runner is indoors, may enable her to more easily and quickly read the display.

In some examples, an estimated physical exertion level of a user may be utilized to update the default brightness setting to a brighter light output level. For example, a user may be engaged in a strenuous physical activity, such as chopping wood, shoveling snow, playing soccer, etc. Often strenuous activities are performed outdoors. Additionally and as noted above, a user engaged in a strenuous activity may desire to quickly check information displayed by the wearable computing device 200. Accordingly, the display brightness program 12 may be configured to, based on receiving heart rate data from a heart rate system comprising heart rate sensor 224 indicating a heart rate above a predetermined exertion level, update the default brightness setting to the updated default brightness setting corresponding to the outdoor light output level.

In some examples, a barometric pressure profile measured by a barometer may be utilized to update the default brightness setting to a brighter light output level. For example, barometric pressure profiles generated when the wearable computing device 200 is indoors are different from barometric pressure profiles when the device is outdoors. In particular, when the device 200 is outdoors, a barometric pressure profile measured by the barometer 252 will have more fluctuation in the signal than a barometric pressure profile measured by the barometer when the device is indoors. Thus, when the wearable computing device 200 is outdoors, the measured barometric pressure profile has a lower signal to noise ratio than a profile measured when the device is indoors. Accordingly, the display brightness program 12 may be configured to, based on receiving barometric pressure data from the barometer indicating that the device is outdoors, update the default brightness setting to the updated default brightness setting corresponding to the outdoor light output level.

In some examples and as noted above, the computing device 10 of wearable computing device 200 may comprise one or more applications, such as an athletic activity program 38. In some examples an athletic activity application may comprise an athletic activity tracking application that may monitor data related to activities such as running, cycling, swimming, gym activities, etc. When using such an athletic activity program 38, a wearer of the wearable computing device 200 may be engaged in an athletic activity. Accordingly, the display brightness program 12 may be configured to determine that an athletic activity application is launching and, based on determining that the athletic activity application is launching, may update the default brightness setting to the updated default brightness setting corresponding to the outdoor light output level.

In some examples, the microphone 260 of wearable computing device 200 may be utilized to update the default brightness setting. More particularly, sound pressure may be measured by microphone 260. Sound pressures are often lower outdoors than indoors because sound is dissipated more easily outdoors. In some examples, a predetermined sound pressure threshold may be utilized such that measured sound pressures below such threshold may indicate that the wearable computing device 200 is outdoors. Accordingly, the display brightness program 12 may be configured to, based on receiving a sound pressure signal that is below a predetermined sound pressure threshold, update the default brightness setting to the updated default brightness setting corresponding to the outdoor light output level.

Figure 4B:
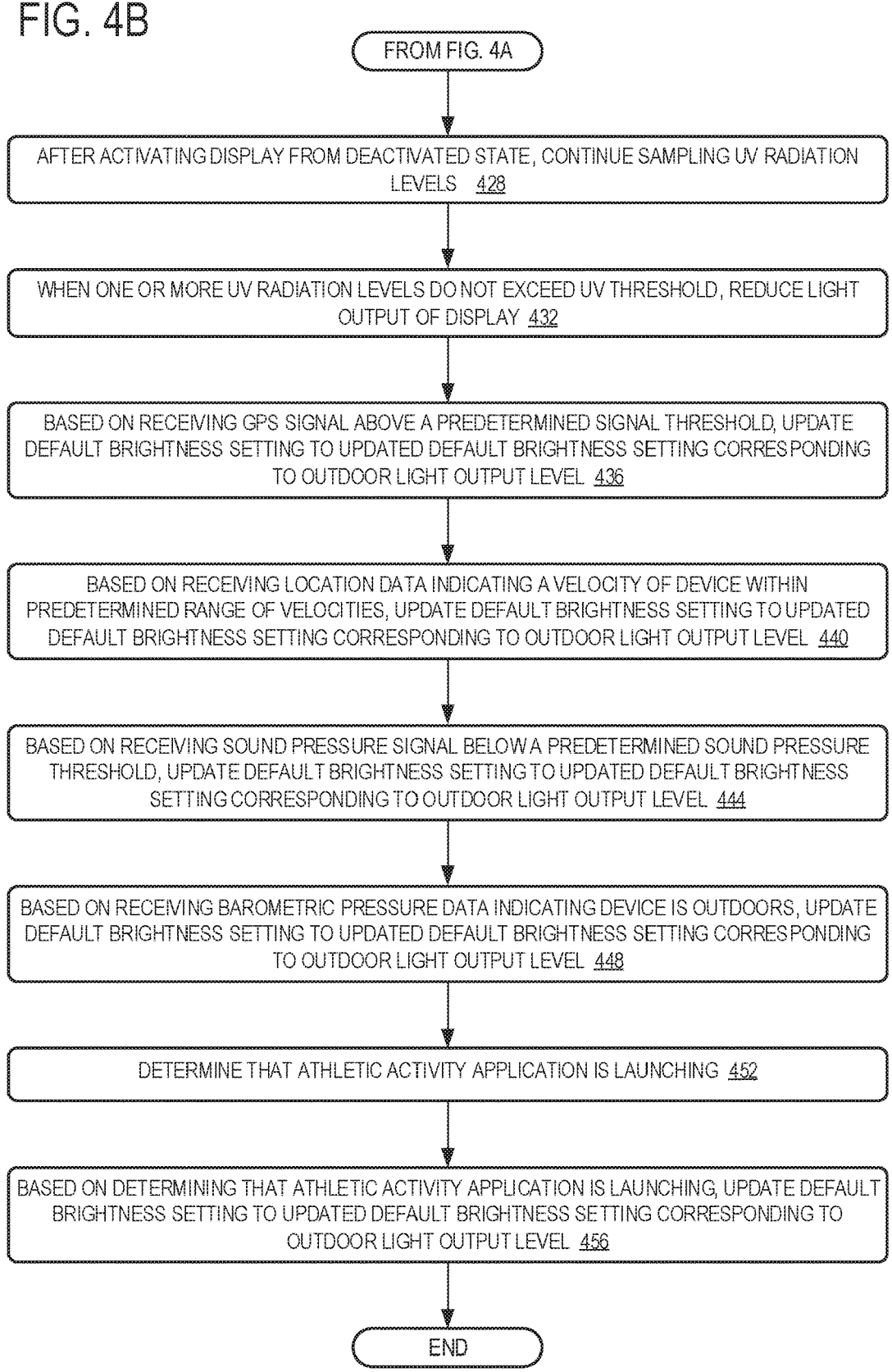

FIGS. 4A and 4B illustrate a flow chart of a method 400 for controlling light output of a display in a computing device according to an example of the present disclosure. The following description of method 400 is provided with reference to the software and hardware components described above and shown in FIGS. 1-3. It will be appreciated that method 400 also may be performed in other contexts using other suitable hardware and software components.

With reference to FIG. 4A, at 404 the method 400 may include setting a default brightness setting in a memory of the computing device to an indoor light output level. At 408 the method 400 may include activating a UV light sensor to detect UV radiation levels. At 412 the method 400 may include, based on determining that one or more of the UV radiation levels exceed a UV threshold, updating the default brightness setting to an updated default brightness setting that corresponds to an outdoor light output level that is greater than the indoor light output level. At 416 the method 400 may include setting a magnitude of the outdoor light output level from a plurality of possible magnitudes based on the one or more UV radiation levels.

At 420 the method 400 may include, without using information from an ambient light sensor, activating the display from a deactivated state to illuminate at the updated default brightness setting corresponding to the outdoor light output level. At 424 the method 400 may include, wherein a default display dimming period is stored in the memory, and based on determining that the one or more UV radiation levels exceed the UV threshold, updating the default display dimming period to an updated default display dimming period that is shorter than the default display dimming period, and after activating the display from the deactivated state at an activation time, reducing a light output of the display upon an expiration of the updated default display dimming period as measured from the activation time.

With reference now to FIG. 4B, at 428 the method 400 may include, after activating the display from the deactivated state, continuing to sample the UV radiation levels. At 432 the method 400 may include, when one or more of the UV radiation levels do not exceed the UV threshold, reducing a light output of the display. At 436 the method 400 may include, based on receiving a GPS signal that is above a predetermined signal threshold, updating the default brightness setting to the updated default brightness setting corresponding to the outdoor light output level. At 440 the method 400 may include, based on receiving location data that indicates a velocity of the device within a predetermined range of velocities, updating the default brightness setting to the updated default brightness setting corresponding to the outdoor light output level.

At 444 the method 400 may include, based on receiving a sound pressure signal that is below a predetermined sound pressure threshold, updating the default brightness setting to the updated default brightness setting corresponding to the outdoor light output level. At 448 the method 400 may include, based on receiving barometric pressure data indicating that the device is outdoors, updating the default brightness setting to the updated default brightness setting corresponding to the outdoor light output level. At 452 the method 400 may include determining that an athletic activity application is launching. At 456 the method 400 may include, based on determining that the athletic activity application is launching, updating the default brightness setting to the updated default brightness setting corresponding to the outdoor light output level.

It will be appreciated that method 400 is provided by way of example and is not meant to be limiting. Therefore, it is to be understood that method 400 may include additional and/or alternative steps relative to those illustrated in FIGS. 4A and 4B. Further, it is to be understood that method 400 may be performed in any suitable order. Further still, it is to be understood that one or more steps may be omitted from method 400 without departing from the scope of this disclosure.

In some embodiments, the methods and processes described herein may be tied to a computing system of one or more computing devices. In particular, such methods and processes may be implemented as a computer-application program or service, an application-programming interface (API), a library, and/or other computer-program product.

Figure 5:
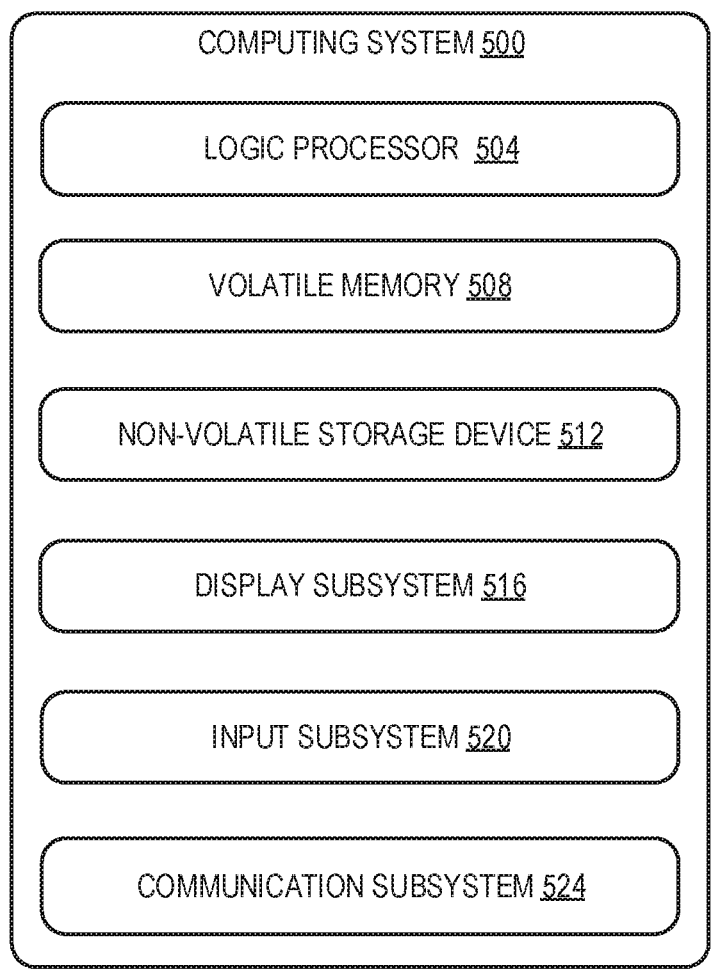
FIG. 5 schematically shows a computing system according to examples of the present disclosure.

FIG. 5 schematically shows a non-limiting embodiment of a computing system 500 that can enact one or more of the methods and processes described above. Computing system 500 is shown in simplified form. Computing device 10 shown in FIG. 1 and FIG. 2B may take the form of computing system 500.

Computing system 500 includes a logic processor 504, volatile memory 508, and a non-volatile storage device 512. Computing system 500 may optionally include a display subsystem 516, input subsystem 520, communication subsystem 524, and/or other components not shown in FIG. 5.

Logic processor 504 includes one or more physical devices configured to execute instructions. For example, the logic processor may be configured to execute instructions that are part of one or more applications, programs, routines, libraries, objects, components, data structures, or other logical constructs. Such instructions may be implemented to perform a task, implement a data type, transform the state of one or more components, achieve a technical effect, or otherwise arrive at a desired result.

The logic processor 504 may include one or more physical processors (hardware) configured to execute software instructions. Additionally or alternatively, the logic processor may include one or more hardware logic circuits or firmware devices configured to execute hardware-implemented logic or firmware instructions. Processors of the logic processor 504 may be single-core or multi-core, and the instructions executed thereon may be configured for sequential, parallel, and/or distributed processing. Individual components of the logic processor optionally may be distributed among two or more separate devices, which may be remotely located and/or configured for coordinated processing. Aspects of the logic processor 504 may be virtualized and executed by remotely accessible, networked computing devices configured in a cloud-computing configuration. In such a case, these virtualized aspects may be run on different physical logic processors of various different machines.

Volatile memory 508 may include physical devices that include random access memory. Volatile memory 508 is typically utilized by logic processor 504 to temporarily store information during processing of software instructions. It will be appreciated that volatile memory 508 typically does not continue to store instructions when power is cut to the volatile memory.

Non-volatile storage device 512 includes one or more physical devices configured to hold instructions executable by the logic processors to implement the methods and processes described herein. When such methods and processes are implemented, the state of non-volatile storage device 512 may be transformed—e.g., to hold different data.

Non-volatile storage device 512 may include physical devices that are removable and/or built-in. Non-volatile storage device 512 may include optical memory (CD, DVD, HD-DVD, Blu-Ray Disc, etc.), semiconductor memory (ROM, EPROM, EEPROM, FLASH memory, etc.), and/or magnetic memory (hard-disk drive, floppy-disk drive, tape drive, MRAM, etc.), or other mass storage device technology. Non-volatile storage device 512 may include nonvolatile, dynamic, static, read/write, read-only, sequential-access, location-addressable, file-addressable, and/or content-addressable devices. It will be appreciated that non-volatile storage device 512 is configured to hold instructions even when power is cut to the non-volatile storage device.

Aspects of logic processor 504, volatile memory 508, and non-volatile storage device 512 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The term "program" may be used to describe an aspect of computing system 500 implemented to perform a particular function. In some cases, a program may be instantiated via logic processor 504 executing instructions held by non-volatile storage device 512, using portions of volatile memory 508. It will be understood that different programs may be instantiated from the same application, service, code block, object, library, routine, API, function, etc. Likewise, the same program may be instantiated by different applications, services, code blocks, objects, routines, APIs, functions, etc. The term "program" encompasses individual or groups of executable files, data files, libraries, drivers, scripts, database records, etc.

When included, display subsystem 516 may be used to present a visual representation of data held by non-volatile storage device 512. As the herein described methods and processes change the data held by the non-volatile storage device, and thus transform the state of the non-volatile storage device, the state of display subsystem 516 may likewise be transformed to visually represent changes in the underlying data. Display subsystem 516 may include one or more display devices utilizing virtually any type of technology. Such display devices may be combined with logic processor 504, volatile memory 508, and/or non-volatile storage device 512 in a shared enclosure, or such display devices may be peripheral display devices.

When included, input subsystem 520 may comprise or interface with one or more user-input devices. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection, gaze detection, and/or intent recognition; electric-field sensing componentry for assessing brain activity; any of the sensors described above with respect to wearable computing device 200; and/or any other suitable sensor.

When included, communication subsystem 524 may be configured to communicatively couple computing system 500 with one or more other computing devices. Communication subsystem 524 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 500 to send and/or receive messages to and/or from other devices via a network such as the Internet.

The following paragraphs provide additional support for the claims of the subject application. One aspect provides a computing device, comprising: a display; a UV light sensor; a memory storing a default brightness setting; a processor; and a display brightness program executable by the processor, the display brightness program configured to: set the default brightness setting to an indoor light output level; activate the UV light sensor to detect UV radiation levels; based on determining that one or more of the UV radiation levels exceed a UV threshold, update the default brightness setting to an updated default brightness setting that corresponds to an outdoor light output level that is greater than the indoor light output level; and activate the display from a deactivated state to illuminate at the updated default brightness setting corresponding to the outdoor light output level. The computing device may additionally or alternatively include, wherein the display brightness program is further configured to set a magnitude of the outdoor light output level from a plurality of possible magnitudes based on the one or more UV radiation levels. The computing device may additionally or alternatively include, wherein a default display dimming period is stored in the memory, and the display brightness program is further configured to: based on determining that the one or more UV radiation levels exceed the UV threshold: update the default display dimming period to an updated default display dimming period that is shorter than the default display dimming period; and after activating the display from the deactivated state at an activation time, reduce a light output of the display upon an expiration of the updated default display dimming period as measured from the activation time. The computing device may additionally or alternatively include, wherein the display brightness program is further configured to: after activating the display from the deactivated state, continue sampling the UV radiation levels; and when one or more of the UV radiation levels do not exceed the UV threshold, reduce a light output of the display. The computing device may additionally or alternatively include a GPS system, wherein the display brightness program is further configured to, based on receiving a GPS signal from the GPS system that is above a predetermined signal threshold, update the default brightness setting to the updated default brightness setting corresponding to the outdoor light output level. The computing device may additionally or alternatively include a GPS system, wherein the display brightness program is further configured to, based on receiving location data from the GPS system that indicates a velocity of the device within a predetermined range of velocities, update the default brightness setting to the updated default brightness setting corresponding to the outdoor light output level. The computing device may additionally or alternatively include a heart rate sensor system, and the display brightness program is further configured to, based on receiving heart rate data from the heart rate sensor system indicating a heart rate above a predetermined exertion level, update the default brightness setting to the updated default brightness setting corresponding to the outdoor light output level. The computing device may additionally or alternatively include a barometer, and the display brightness program is further configured to, based on receiving barometric pressure data from the barometer indicating that the device is outdoors, update the default brightness setting to the updated default brightness setting corresponding to the outdoor light output level. The computing device may additionally or alternatively include an athletic activity application stored in the memory, wherein the display brightness program is further configured to: determine that the athletic activity application is launching; and based on determining that the athletic activity application is launching, update the default brightness setting to the updated default brightness setting corresponding to the outdoor light output level.

Another aspect provides a method for controlling light output of a display in a computing device, the method comprising: setting a default brightness setting in a memory of the computing device to an indoor light output level; activating a UV light sensor to detect UV radiation levels; based on determining that one or more of the UV radiation levels exceed a UV threshold, updating the default brightness setting to an updated default brightness setting that corresponds to an outdoor light output level that is greater than the indoor light output level; and without using information from an ambient light sensor, activating the display from a deactivated state to illuminate at the updated default brightness setting corresponding to the outdoor light output level. The method may additionally or optionally include setting a magnitude of the outdoor light output level from a plurality of possible magnitudes based on the one or more UV radiation levels. The method may additionally or optionally include, wherein a default display dimming period is stored in the memory, the method further comprising: based on determining that the one or more UV radiation levels exceed the UV threshold: updating the default display dimming period to an updated default display dimming period that is shorter than the default display dimming period; and after activating the display from the deactivated state at an activation time, reducing a light output of the display upon an expiration of the updated default display dimming period as measured from the activation time. The method may additionally or optionally include, after activating the display from the deactivated state, continuing to sample the UV radiation levels; and when one or more of the UV radiation levels do not exceed the UV threshold, reducing a light output of the display. The method may additionally or optionally include, based on receiving a GPS signal that is above a predetermined signal threshold, updating the default brightness setting to the updated default brightness setting corresponding to the outdoor light output level. The method may additionally or optionally include, based on receiving location data that indicates a velocity of the computing device within a predetermined range of velocities, updating the default brightness setting to the updated default brightness setting corresponding to the outdoor light output level. The method may additionally or optionally include, based on receiving a sound pressure signal that is below a predetermined sound pressure threshold, updating the default brightness setting to the updated default brightness setting corresponding to the outdoor light output level. The method may additionally or optionally include, based on receiving barometric pressure data indicating that the device is outdoors, updating the default brightness setting to the updated default brightness setting corresponding to the outdoor light output level. The method may additionally or optionally include determining that an athletic activity application is launching; and based on determining that the athletic activity application is launching, updating the default brightness setting to the updated default brightness setting corresponding to the outdoor light output level.

Another aspect provides wearable computing device, comprising: a display; an ambient light sensor; a UV light sensor; a memory storing a default brightness setting and a default display dimming period; a processor; and a display brightness program executable by the processor, the display brightness program configured to: set the default brightness setting to an indoor light output level; activate the UV light sensor to detect UV radiation levels; based on determining that one or more of the UV radiation levels exceed a UV threshold: update the default brightness setting to an updated default brightness setting that corresponds to an outdoor light output level that is greater than the indoor light output level; and update the default display dimming period to an updated default display dimming period that is shorter than the default display dimming period; without using information from the ambient light sensor and in response to a display activation command at an activation time, activate the display from a deactivated state to illuminate at the updated default brightness setting corresponding to the outdoor light output level; and reduce a light output of the display upon an expiration of the updated default display dimming period as measured from the activation time. The wearable computing device may additionally or alternatively include, wherein the display brightness program is further configured to set a magnitude of the outdoor light output level from a plurality of possible magnitudes based on the one or more UV radiation levels.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A computing device, comprising:
   a display;
   a UV light sensor;
   a memory storing a default brightness setting;
   a processor; and
   a display brightness program executable by the processor, the display brightness program configured to:
      set the default brightness setting to an indoor light output level;
      activate the UV light sensor to detect UV radiation levels;
      while the display is deactivated, determine that one or more of the UV radiation levels goes above a UV threshold;
      based on determining that one or more of the UV radiation levels goes above the UV threshold, update the default brightness setting to an updated default brightness setting that corresponds to an outdoor light output level that is greater than the indoor light output level;
      activate the display from the deactivated state to illuminate at the updated default brightness setting corresponding to the outdoor light output level; and
      wherein the UV threshold is a positive non-zero value.

2. The computing device of claim 1, wherein the display brightness program is further configured to set a magnitude of the outdoor light output level from a plurality of possible magnitudes based on the one or more UV radiation levels.

3. The computing device of claim 1, wherein a default display dimming period is stored in the memory, and the display brightness program is further configured to:
   based on determining that the one or more UV radiation levels goes above the UV threshold:
      update the default display dimming period to an updated default display dimming period that is shorter than the default display dimming period; and
      after activating the display from the deactivated state at an activation time, reduce a light output of the display upon an expiration of the updated default display dimming period as measured from the activation time.

4. The computing device of claim 1, wherein the display brightness program is further configured to:
   after activating the display from the deactivated state, continue sampling the UV radiation levels; and
   when one or more of the UV radiation levels do not go above the UV threshold, reduce a light output of the display.

5. The computing device of claim 1, further comprising a GPS system, wherein the display brightness program is further configured to, based on receiving a GPS signal from the GPS system that is above a predetermined signal threshold, update the default brightness setting to the updated default brightness setting corresponding to the outdoor light output level.

6. The computing device of claim 1, further comprising a GPS system, wherein the display brightness program is further configured to, based on receiving location data from the GPS system that indicates a velocity of the device within a predetermined range of velocities, update the default brightness setting to the updated default brightness setting corresponding to the outdoor light output level.

7. The computing device of claim 1, wherein the computing device comprises a heart rate sensor system, and the display brightness program is further configured to, based on receiving heart rate data from the heart rate sensor system indicating a heart rate above a predetermined exertion level, update the default brightness setting to the updated default brightness setting corresponding to the outdoor light output level.

8. The computing device of claim 1, wherein the computing device comprises a barometer, and the display brightness program is further configured to, based on receiving barometric pressure data from the barometer indicating that the device is outdoors, update the default brightness setting to the updated default brightness setting corresponding to the outdoor light output level.

9. The computing device of claim 1, further comprising an athletic activity application stored in the memory, wherein the display brightness program is further configured to:
determine that the athletic activity application is launching; and
based on determining that the athletic activity application is launching, update the default brightness setting to the updated default brightness setting corresponding to the outdoor light output level.

10. A method for controlling light output of a display in a computing device, the method comprising:
setting a default brightness setting in a memory of the computing device to an indoor light output level;
activating a UV light sensor to detect UV radiation levels;
while the display is deactivated, determining that one or more of the UV radiation levels goes above a UV threshold;
based on determining that one or more of the UV radiation levels goes above the UV threshold, updating the default brightness setting to an updated default brightness setting that corresponds to an outdoor light output level that is greater than the indoor light output level;
without using information from an ambient light sensor, activating the display from the deactivated state to illuminate at the updated default brightness setting corresponding to the outdoor light output level; and
wherein the UV threshold is a positive non-zero value.

11. The method of claim 10, further comprising setting a magnitude of the outdoor light output level from a plurality of possible magnitudes based on the one or more UV radiation levels.

12. The method of claim 10, wherein a default display dimming period is stored in the memory, the method further comprising:
based on determining that the one or more UV radiation levels goes above the UV threshold:
updating the default display dimming period to an updated default display dimming period that is shorter than the default display dimming period; and
after activating the display from the deactivated state at an activation time, reducing a light output of the display upon an expiration of the updated default display dimming period as measured from the activation time.

13. The method of claim 10, further comprising:
after activating the display from the deactivated state, continuing to sample the UV radiation levels; and
when one or more of the UV radiation levels do not go above the UV threshold, reducing a light output of the display.

14. The method of claim 10, further comprising, based on receiving a GPS signal that is above a predetermined signal threshold, updating the default brightness setting to the updated default brightness setting corresponding to the outdoor light output level.

15. The method of claim 10, further comprising, based on receiving location data that indicates a velocity of the computing device within a predetermined range of velocities, updating the default brightness setting to the updated default brightness setting corresponding to the outdoor light output level.

16. The method of claim 10, further comprising, based on receiving a sound pressure signal that is below a predetermined sound pressure threshold, updating the default brightness setting to the updated default brightness setting corresponding to the outdoor light output level.

17. The method of claim 10, further comprising, based on receiving barometric pressure data indicating that the device is outdoors, updating the default brightness setting to the updated default brightness setting corresponding to the outdoor light output level.

18. The method of claim 10, further comprising:
determining that an athletic activity application is launching; and
based on determining that the athletic activity application is launching, updating the default brightness setting to the updated default brightness setting corresponding to the outdoor light output level.

19. A wearable computing device, comprising:
a display;
an ambient light sensor;
a UV light sensor;
a memory storing a default brightness setting and a default display dimming period;
a processor; and
a display brightness program executable by the processor, the display brightness program configured to:
set the default brightness setting to an indoor light output level;
activate the UV light sensor to detect UV radiation levels;
while the display is deactivated, determine that one or more of the UV radiation levels goes above a UV threshold;
based on determining that one or more of the UV radiation levels goes above the UV threshold:
update the default brightness setting to an updated default brightness setting that corresponds to an outdoor light output level that is greater than the indoor light output level; and
update the default display dimming period to an updated default display dimming period that is shorter than the default display dimming period;
without using information from the ambient light sensor and in response to a display activation command at an activation time, activate the display from the deactivated state to illuminate at the updated default brightness setting corresponding to the outdoor light output level;
reduce a light output of the display upon an expiration of the updated default display dimming period as measured from the activation time; and
wherein the UV threshold is a positive non-zero value.

20. The wearable computing device of claim 19, wherein the display brightness program is further configured to set a magnitude of the outdoor light output level from a plurality of possible magnitudes based on the one or more UV radiation levels.

* * * * *